(12) United States Patent
Usuda et al.

(10) Patent No.: US 10,165,952 B2
(45) Date of Patent: Jan. 1, 2019

(54) BIOLOGICAL INFORMATION MEASURING APPARATUS AND BIOLOGICAL INFORMATION MEASURING METHOD

(71) Applicant: NIHON KOHDEN CORPORATION, Tokyo (JP)

(72) Inventors: Takashi Usuda, Tokyo (JP); Hiroshi Kubo, Tokyo (JP); Yukio Koyama, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 691 days.

(21) Appl. No.: 14/799,040

(22) Filed: Jul. 14, 2015

(65) Prior Publication Data

US 2016/0029908 A1 Feb. 4, 2016

(30) Foreign Application Priority Data

Jul. 30, 2014 (JP) .................................. 2014-155484

(51) Int. Cl.
*A61B 5/02* (2006.01)
*A61B 5/021* (2006.01)
(Continued)

(52) U.S. Cl.
CPC .......... *A61B 5/02116* (2013.01); *A61B 5/022* (2013.01); *A61B 5/02225* (2013.01);
(Continued)

(58) Field of Classification Search
CPC ... A61B 5/02225; A61B 5/022; A61B 5/7278; A61B 5/02116
See application file for complete search history.

(56) References Cited

U.S. PATENT DOCUMENTS 5,365,933 A 11/1994 Elghazzawi
2005/0148812 A1 7/2005 Nigroni et al.
(Continued)

FOREIGN PATENT DOCUMENTS

JP 61-85922 A 5/1986
JP 8-581 A 1/1996
(Continued)

OTHER PUBLICATIONS

Communication dated Dec. 8, 2015 issued by European Patent Office in counterpart European Patent Application No. 15176736.5.
(Continued)

*Primary Examiner* — Christian Jang
(74) *Attorney, Agent, or Firm* — Sughrue Mion, PLLC (57) ABSTRACT

A biological information measuring apparatus and method are provided. A pulsation information detecting unit detects heartbeat information relating to a heartbeat of a subject. A pulse wave detecting unit detects a pulse wave while a portion of the subject is pressurized and depressurized by a cuff. An amplitude calculating unit detects a cardiac cycle of a heart from the heartbeat information and a maximal value of the pulse wave in each cardiac cycle, and calculates, based on the maximal value detected from the pulse wave, at least one of an amplitude value derived from the heartbeat of the subject, an amplitude value assisted by an IABP, and an amplitude value derived from a blood flow volume of the subject. A blood pressure calculating unit calculates a blood pressure value from a relationship between the amplitude values calculated by the amplitude calculating unit and a pressurizing force of the cuff.

10 Claims, 10 Drawing Sheets

(51) Int. Cl.
*A61B 5/022* (2006.01)
*A61B 5/0402* (2006.01)
*A61B 5/00* (2006.01)
*A61M 1/10* (2006.01)
*A61M 1/12* (2006.01)

(52) U.S. Cl.
CPC .......... *A61B 5/0402* (2013.01); *A61B 5/4851* (2013.01); *A61B 5/7278* (2013.01); *A61M 1/106* (2013.01); *A61M 1/1072* (2013.01); *A61M 1/1086* (2013.01); *A61M 1/122* (2014.02); *A61M 1/125* (2014.02); *A61M 2205/3334* (2013.01)

(56) References Cited

U.S. PATENT DOCUMENTS

2005/0261597 A1    11/2005   Kolluri et al.
2009/0112104 A1     4/2009   Usuda et al.

FOREIGN PATENT DOCUMENTS

| JP | 2007503883 A | 3/2007 |
| JP | 2009-106610 A | 5/2009 |
| WO | 86/03114 A1 | 6/1986 |

OTHER PUBLICATIONS

El-Ghazzawi et al., "An algorithm to extract blood-pressure waveform features during intra-aortic balloon pump assist", Anesthesia Technology, Nov. 9 1989, 2 pages total, Boston, USA.

Communication dated Oct. 12, 2017, from the Japanese Patent Office in counterpart application No. 2014-155484.

BIOLOGICAL INFORMATION MEASURING APPARATUS AND BIOLOGICAL INFORMATION MEASURING METHOD

CROSS-REFERENCE TO RELATED APPLICATION(S)

The present application claims priority from Japanese Patent Application No. 2014-155484 filed on Jul. 30, 2014, the entire content of which is incorporated herein by reference.

BACKGROUND

The presently disclosed subject matter relates to a biological information measuring apparatus and a biological information measuring method for a non-invasive blood pressure measurement.

An intra-aortic balloon pumping (IABP) is a circulation assisting apparatus which is widely used for a left ventricle. In an IABP, a balloon catheter is placed in the thoracic descending aorta of a subject, and the balloon is inflated and deflated in synchronization with the pulsation of the heart to pressure-assist the heart to increase oxygen supply to the cardiac muscle and to reduce oxygen consumption by the cardiac muscle.

For example, JP2007-503883A discloses an apparatus having a function of optimally setting the treatment timing of an IABP.

A blood pressure value is an important vital sign for understanding the condition of the subject. Therefore, it is preferable, also during use of an IABP, to correctly know the blood pressure value of the subject. Hereinafter, the non-invasive blood pressure (NIBP) measurement will be discussed.

In the non-invasive blood pressure measurement, a cuff (manchette) is wrapped around the upper arm or the like of the subject, and the upper arm and also the artery passing inside the upper arm are compressed by the air sent into the cuff. The pulsation of the compressed artery is transmitted as vibrations to the cuff (oscillation), and the blood pressure value is calculated from the degree of the vibrations. In a case where the subject uses an IABP, however, a blood pressure value calculated based on the balloon-assisted heartbeat (e.g., a systolic pressure (SYS), a diastolic pressure (DIA) and a mean arterial pressure (MAP)) and a blood pressure value calculated based on the unassisted heartbeat of the subject (e.g., a systolic pressure (SYS), a diastolic pressure (DIA) and a mean arterial pressure (MAP)) cannot be distinguished from one another. Accordingly, the blood pressure values cannot be obtained accurately.

SUMMARY

Illustrative aspects of the present invention provide a biological information measuring apparatus and a biological information measuring method according to which blood pressure values of a subject, such as a blood pressure value derived from a heartbeat of the subject, a blood pressure value assisted by an IABP, and an amplitude value derived from the blood flow volume, can be obtained accurately even when the subject may be using the IABP.

According to an illustrative aspect of the present invention, a biological information measuring apparatus includes a pulsation information detecting unit configured to detect heartbeat information relating to a heartbeat of a subject, a pulse wave detecting unit configured to detect a pulse wave of the subject during a time period in which a cuff is inflated to pressurize a portion of the subject and during a time period in which the cuff is deflated to depressurize the portion of the subject, an amplitude calculating unit configured to detect a cardiac cycle of a heart from the heartbeat information and a maximal value of the pulse wave in each cardiac cycle, and to calculate, based on the maximal value detected from the pulse wave, at least one of an amplitude value derived from the heartbeat of the subject, an amplitude value assisted by an IABP, and an amplitude value derived from a blood flow volume of the subject, and a blood pressure calculating unit configured to calculate a blood pressure value from a relationship between the amplitude values calculated by the amplitude calculating unit and a pressurizing force of the cuff.

According to another illustrative aspect of the present invention, a biological information measuring method includes detecting heartbeat information relating to a heartbeat of a subject, detecting a pulse wave of the subject during a time period in which a cuff is inflated to pressurize a portion of the subject and during a time period in which the cuff is deflated to depressurize the portion of the subject, detecting a cardiac cycle of a heart from the heartbeat information and a maximal value of the pulse wave in each cardiac cycle, calculating, at least one of an amplitude value derived from the heartbeat of the subject, an amplitude value assisted by an IABP, and an amplitude value derived from a blood flow volume of the subject, based on the maximal value detected from the pulse wave, and calculating a blood pressure value from a relationship between the calculated amplitude values and a pressurizing force of the cuff.

According to another illustrative aspect of the present invention, a non-transitory computer readable medium stores a program that, when executed by a computer, causes the computer to execute a method including detecting heartbeat information relating to a heartbeat of a subject, detecting a pulse wave of the subject during a time period in which a cuff is inflated to pressurize a portion of the subject and during a time period in which the cuff is deflated to depressurize the portion of the subject, detecting a cardiac cycle of a heart from the heartbeat information and a maximal value of the pulse wave in each cardiac cycle, calculating at least one of an amplitude value derived from the heartbeat of the subject, an amplitude value assisted by an IABP, and an amplitude value derived from a blood flow volume of the subject, based on the maximal value detected from the pulse wave, and calculating a blood pressure value from a relationship between the calculated amplitude values and a pressurizing force of the cuff.

According to another illustrative aspect of the present invention, a program causes a computer to execute a method including detecting heartbeat information relating to a heartbeat of a subject, detecting a pulse wave of the subject during a time period in which a cuff is inflated to pressurize a portion of the subject and during a time period in which the cuff is deflated to depressurize the portion of the subject, detecting a cardiac cycle of a heart from the heartbeat information and a maximal value of the pulse wave in each cardiac cycle, calculating at least one of an amplitude value derived from the heartbeat of the subject, an amplitude value assisted by an IABP, and an amplitude value derived from a blood flow volume of the subject, based on the maximal value detected from the pulse wave, and calculating a blood pressure value from a relationship between the calculated amplitude values and a pressurizing force of the cuff.

DETAILED DESCRIPTION

Figure 1:
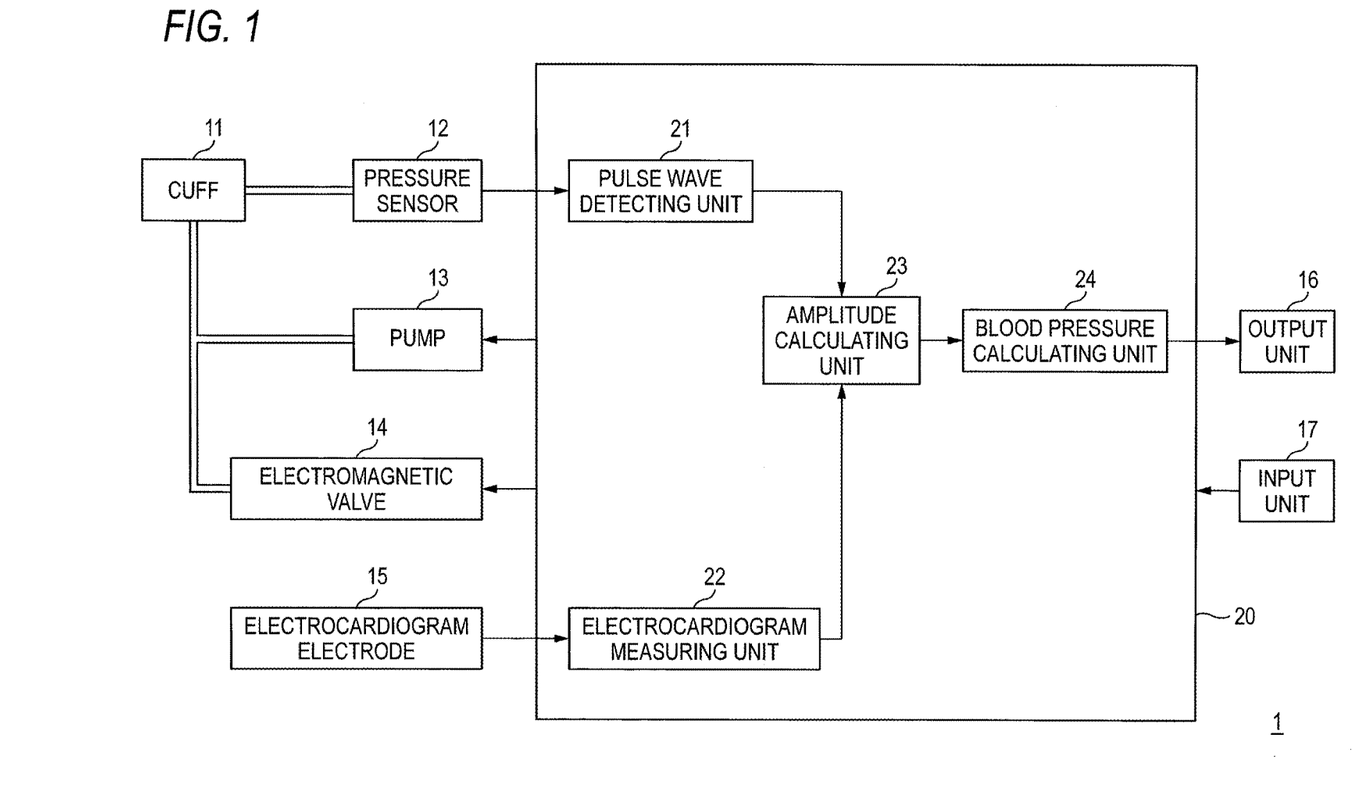
FIG. 1 is a block diagram illustrating a configuration of a biological information measuring apparatus according to an exemplary embodiment of the present invention.

Hereinafter, an exemplary embodiment of the invention will be described with reference to the drawings. FIG. 1 is a block diagram showing the configuration of a biological information measuring apparatus 1 of the exemplary embodiment. The biological information measuring apparatus 1 has a cuff 11, a pressure sensor 12, a pump 13, an electromagnetic valve 14, an electrocardiogram electrode 15, an output unit 16, an input unit 17, and a control unit 20. The biological information measuring apparatus 1 is configured to noninvasively measure the blood pressure. The biological information measuring apparatus 1 may be configured to obtain various parameters in addition to the blood pressure, like a biological information monitor. In the following description, it is assumed that the subject of the biological information measuring apparatus 1 may be using an intra-aortic balloon pumping (IABP).

The cuff 11 is usually wrapped around the upper arm of the subject. In the cuff 11, an air bladder (not shown in FIG. 1) used for injecting air into the cuff 11 to compress the artery of the subject is disposed. The pump 13 injects air into the air bladder according to the control of the control unit 20. The electromagnetic valve 14 controls the evacuation of air from the air bladder in the cuff 11 under the control of the control unit 20.

Figure 2A:
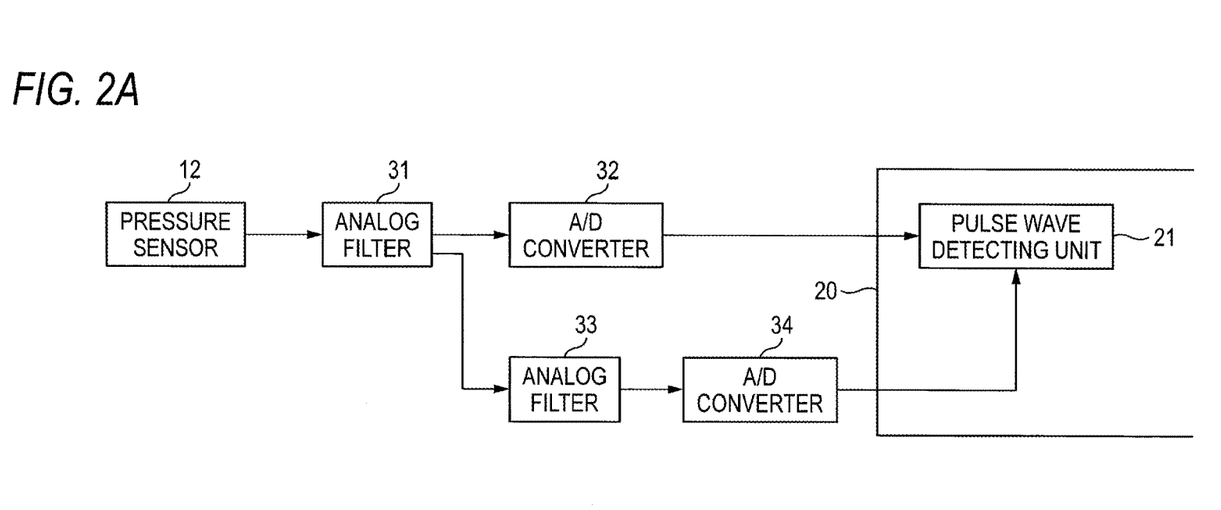
FIG. 2A is another block diagram illustrating a configuration of the biological information measuring apparatus.
Figure 2B:
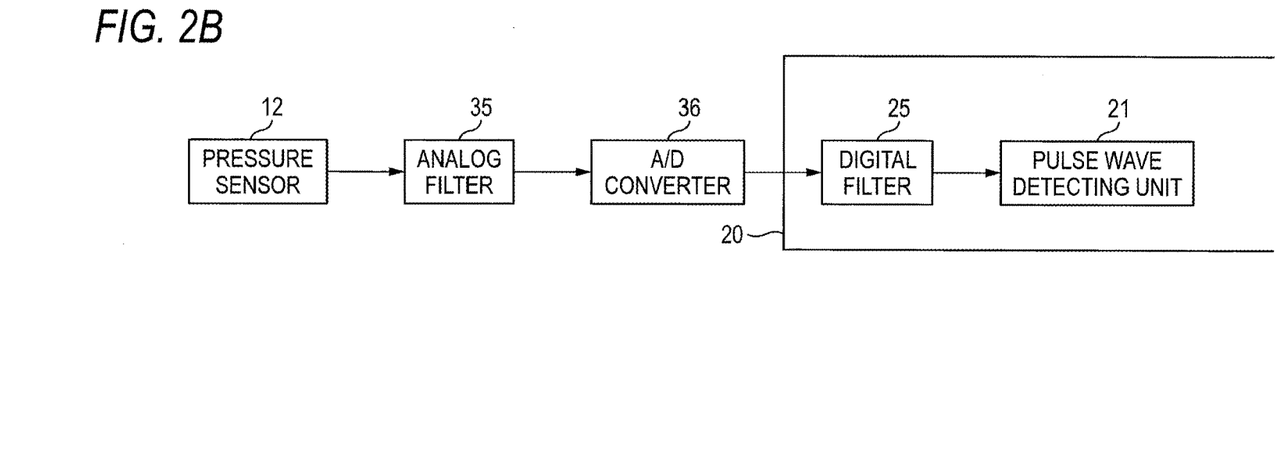
FIG. 2B is another block diagram illustrating a configuration of the biological information measuring apparatus.

The pressure sensor 12 detects the air pressure in the cuff 11, i.e., the cuff pressure. In the subsequent stage of the pressure sensor 12, an A/D converter, an AC amplifier, various filters, and the like are appropriately disposed (not shown in FIG. 1). FIGS. 2A and 2B show examples of the configuration formed between the pressure sensor 12 and a pulse wave detecting unit 21. The configuration of the antecedent stage of the pressure sensor 12, and that of the subsequent stage of the pulse wave detecting unit 21 are not shown in FIGS. 2A and 2B.

FIG. 2A shows a configuration example in the case where filtering is performed mainly by an analog process. An analog filter 31 subsequent to the pressure sensor 12 performs a filtering process to extract an analog signal corresponding to the cuff pressure, and that corresponding to the pulse wave. An AD converter 32 converts the analog signal corresponding to the cuff pressure to a digital signal (cuff pressure signal), and supplies the digital signal to the pulse wave detecting unit 21. The analog signal corresponding to the pulse wave further undergoes a filtering process in an analog filter 33. An A/D converter 34 converts the analog signal output from the analog filter 33 to a digital signal (pulse wave signal), and supplies the digital signal to the pulse wave detecting unit 21.

FIG. 2B shows a configuration example in the case where filtering is performed by using also a digital process. The analog signal output from the pressure sensor 12 undergoes a filtering process in an analog filter 35, and then is input to an A/D converter 36. The A/D converter 36 converts the input analog signal to a digital signal, and supplies the digital signal to a digital filter 25 in the control unit 20. The digital filter 25 performs a digital filtering process on the digital signal to extract a digital signal (cuff pressure signal) corresponding to the cuff pressure, and another digital signal (pulse wave signal) corresponding to the pulse wave of the subject, and supplies the extracted signals to the pulse wave detecting unit 21. The configurations of FIGS. 2A and 2B are merely examples, and any other configuration may be employed in so far as digital values corresponding respectively to the cuff pressure and the pulse wave are supplied to the pulse wave detecting unit 21.

Referring again to FIG. 1, the cuff 11, the pressure sensor 12, the pump 13 and the electromagnetic valve 14 described above are configured in a similar manner as those of a general configuration which is used in non-invasive blood pressure measurements.

The electrocardiogram electrode 15 is includes a plurality of electrodes (including seal electrodes and clip electrodes) which are to be attached to the chest, four limbs, and the like of the subject. The output unit 16 is a display disposed on the housing of the biological information measuring apparatus 1, a built-in printer, or the like. The input unit 17 has various input interfaces arranged on the housing of the biological information measuring apparatus 1, such as buttons and a key panel. The output unit 16 and the input unit 17 may be integrally configured as in a touch display. As described above, the subject may sometimes use an IABP.

The control unit 20 controls the biological information measuring apparatus 1. The control unit 20 includes the pulse wave detecting unit 21, an electrocardiogram measuring unit 22, an amplitude calculating unit 23, and a blood pressure calculating unit 24. The control unit 20 further includes a central processing unit (CPU), ROM (Read Only Memory), random access memory (RAM), I/O (Input/Output) port, hard disk drive, and the like (or devices which operate in a manner coordinated with these devices) which are not shown.

The electrocardiogram measuring unit 22 acquires an ECG (electrocardiogram) based on ECG signals obtained from the electrocardiogram electrode 15, and supplies the acquired ECG to the amplitude calculating unit 23. The operation and configuration of the electrocardiogram measuring unit 22 may be similar to those of a usual electrocardiogram measuring apparatus.

Figure 3:
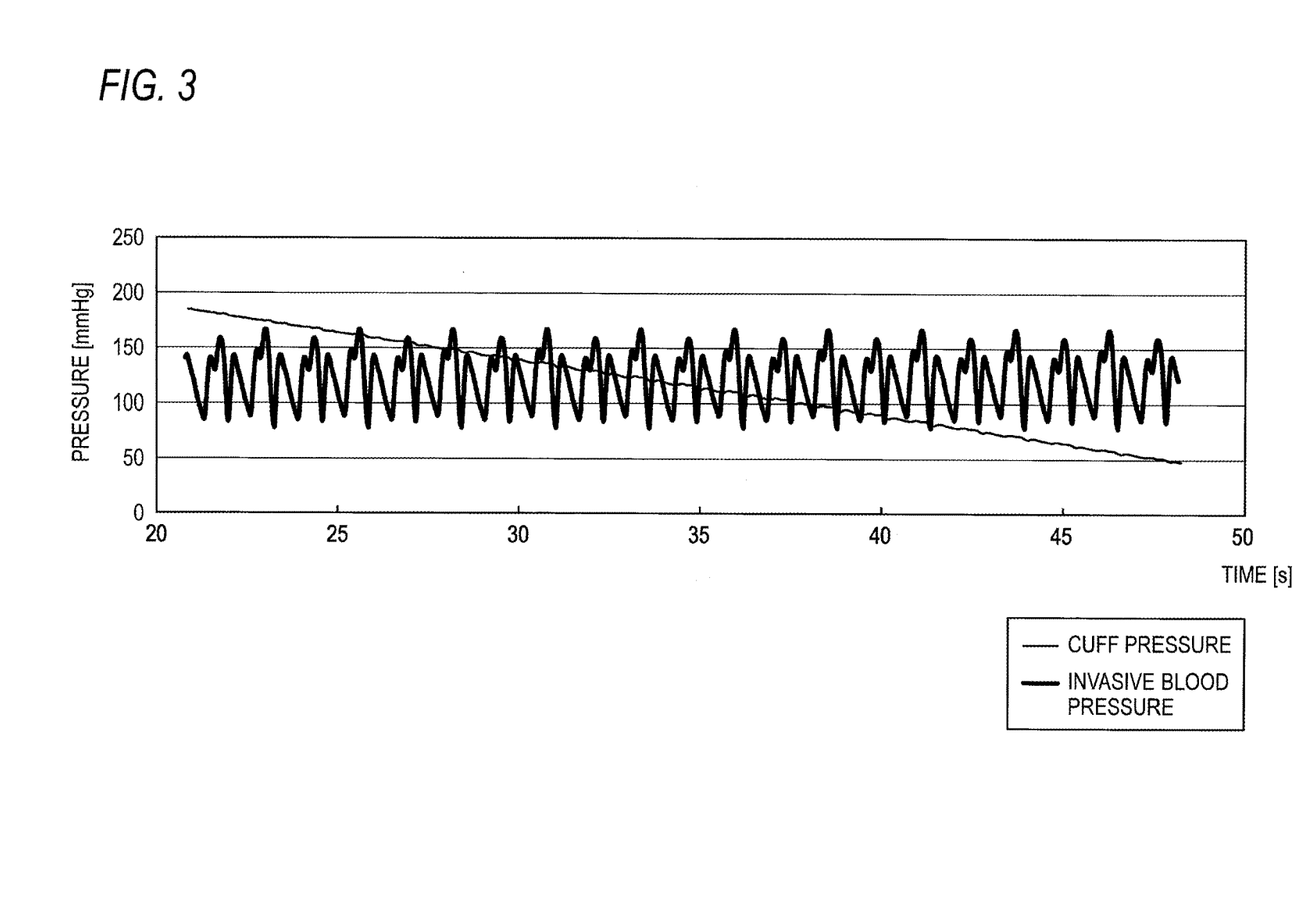
FIG. 3 is a diagram showing a relationship between a cuff pressure produced by a cuff of the biological information measuring apparatus and an invasive blood pressure.

Prior to the description of the operation of the pulse wave detecting unit 21, the relationship between the cuff pressure and the invasive blood pressure (may not be obtained in the apparatus) will be described with reference to FIG. 3. In an example of FIG. 3, the IABP performs a so-called 1:2 assist (during two cardiac cycles, a balloon assist is performed in one of the cardiac cycles).

As illustrated, both a point where the oscillation width (pressure of the pulse wave) is enhanced by the assist of the IABP, and that where the oscillation width (pressure of the pulse wave) is enhanced by the heartbeat of the subject exist in one cardiac cycle of two cardiac cycles.

Figure 4:
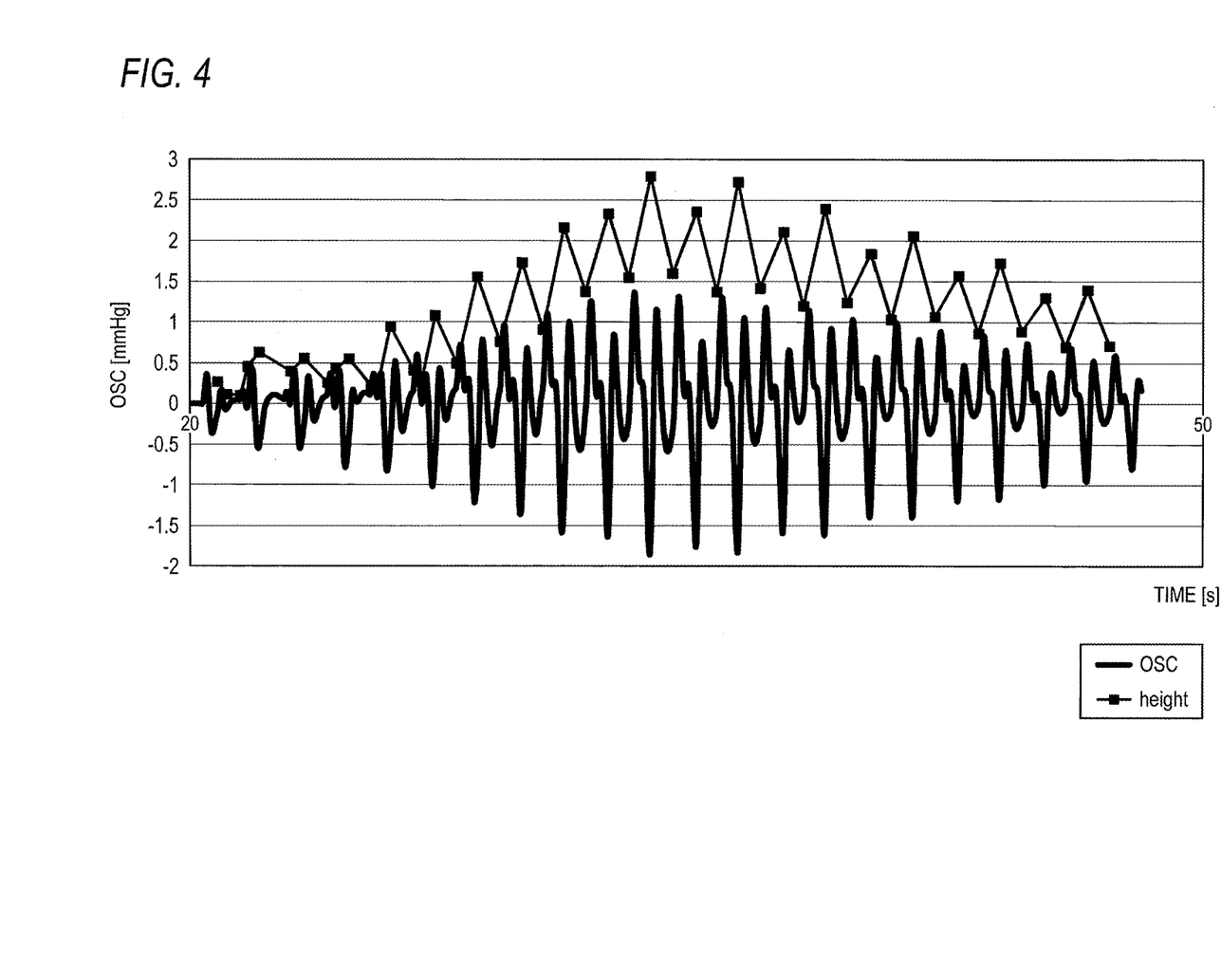
FIG. 4 is a diagram showing pulse waves detected by a pulse wave detecting unit of the biological information measuring apparatus.

Based on the cuff pressure signal (not shown) and the pulse wave signal (not shown), the pulse wave detecting unit 21 detects a pulse wave (hereinafter, may be referred to as "oscillation waveform") of the subject during a time period in which the cuff 11 is inflated to pressurize the subject and during a time period in which the cuff 11 is deflated to depressurize the subject. FIG. 4 shows the oscillation waveform ("OSC" in FIG. 4) detected by the pulse wave detecting unit 21. The oscillation waveform shown in FIG. 4 corresponds to the change of the cuff pressure and invasive blood pressure shown in FIG. 3. The pulse wave detecting unit 21 may also acquire the wave crest value ("height" in FIG. 4) which can be acquired from the oscillation waveform. The pulse wave detecting unit 21 supplies the acquired information (information of the oscillation waveform and the wave crest value) of the pulse wave, and that of the cuff pressure, to the amplitude calculating unit 23.

The information (information of the oscillation waveform and the wave crest value) of the pulse wave which is detected by the pulse wave detecting unit 21, that of the cuff pressure, and the ECG acquired by the electrocardiogram measuring unit 22 are supplied to the amplitude calculating unit 23. The amplitude calculating unit 23 detects a cardiac cycle of the heart of the subject from the heartbeat information (in this example, the ECG). In accordance with detection of a maximal value of the oscillation waveform in one cardiac cycle, then, the amplitude calculating unit 23 calculates the value of an amplitude derived from the heartbeat of the subject or that assisted by the IABP, from the oscillation waveform. The calculating process will be described in detail below.

Figure 5:
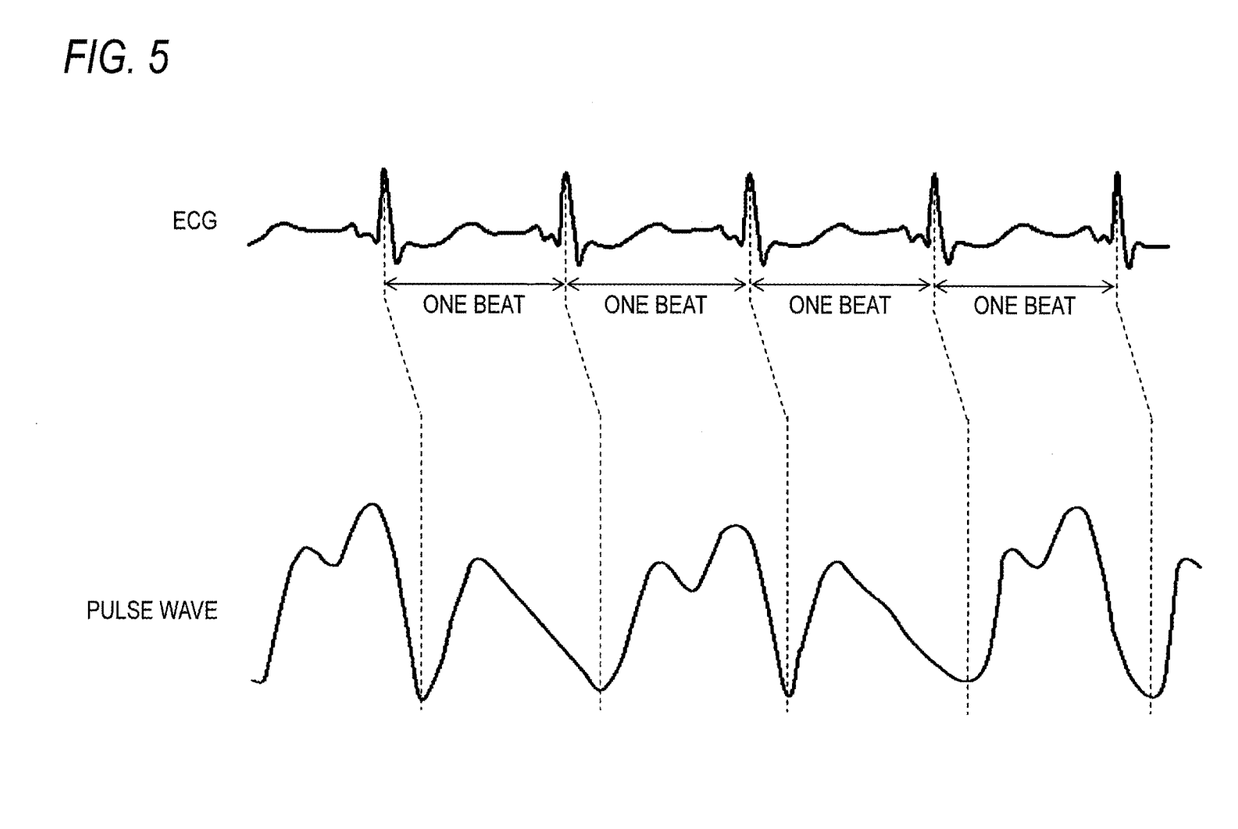
FIG. 5 is a view showing relationships between an ECG waveform and an oscillation waveform.

FIG. 5 is a view showing relationships between the ECG waveform and the oscillation waveform. In the example of FIG. 5, the IABP performs a so-called 1:2 assist (during two cardiac cycles, a balloon assist is performed in one of the cardiac cycles). In the ECG, as illustrated, a QRS wave exists in each beat. The so-called R-R interval corresponds to one cardiac cycle (one heartbeat period). In treatment using an IABP, the balloon is deflated during the systolic phase of the heart of the subject, and, during the diastolic phase, the balloon is inflated at the same time when the aortic valve closes. Usually, the balloon of an IABP is inflated/deflated in synchronization with the blood pressure (blood pressure waveform) or an ECG.

The amplitude calculating unit 23 analyzes the ECG waveform to detect a QRS wave, and acquires the interval of one beat of the heart. As shown in FIG. 5, then, the amplitude calculating unit 23 segments the oscillation waveform of each cardiac cycle with reference to the minimum value of the oscillation waveform within a given time period from the QRS wave.

The amplitude calculating unit 23 detects the maximal value of the oscillation waveform in each cardiac cycle. Here, the maximal value is a point where the amplitude value transitions from ascent to descent. Except in cases of arrhythmia, dicrotic wave, and the like, in the case of a cardiac cycle in which balloon assist is not performed, one maximal value appears in one cardiac cycle. In the case of a cardiac cycle in which balloon assist is performed, two maximal values appear in one cardiac cycle. The amplitude calculating unit 23 does not treat peak points (so-called noises or dicrotic wave) where ascent and descent of the blood pressure value are repeated in a short time period (predetermined time period), as a maximal value. The amplitude calculating unit 23 may perform a filtering process as preprocessing in order to eliminate the influence of noises and the like. The amplitude calculating unit 23 estimates the IABP assist ratio in accordance with situation of detection of a maximal value (the detection number of a maximal value in one cardiac cycle).

The operation in the case where the mode of the IABP is presumed to be 1:n (n being two or more) will be described with reference to FIG. 6. In the case where the mode of the IABP is assumed to be 1:n (n being two or more), the amplitude calculating unit 23 detects the first maximal value in one cardiac cycle where two maximal values appear, as the amplitude value derived from the heartbeat of the subject (according to the operation of the heart of the subject) (FIG. 6, (A)). Moreover, the amplitude calculating unit 23 detects the second maximal value in one cardiac cycle where two maximal values appear, as the amplitude value assisted by the IABP (FIG. 6, (B)). In one cardiac cycle where only one maximal value appears, the amplitude calculating unit 23 detects the maximal value as the amplitude value derived from the heartbeat of the subject (according to the operation of the heart of the subject) (FIG. 6, (A)). Then, the amplitude calculating unit 23 sequentially fetches the amplitude value derived from the heartbeat of the subject, and that assisted by the IABP from each cardiac cycle, and produces an oscillation table (data string) indicating relationships between the elapsed time and the change of the amplitude value (FIG. 6, (B)).

The operation in the case where the mode of the IABP is presumed to be 1:1 will be described with reference to FIG. 7. In the case where the mode of the IABP is presumed to be 1:1, the amplitude calculating unit 23 detects the first maximal value in each cardiac cycle, as the amplitude value derived from the heartbeat of the subject (according to the operation of the heart of the subject) (FIG. 7, (A)). Moreover, the amplitude calculating unit 23 detects the second maximal value in each cardiac cycle, as the amplitude value assisted by the IABP (FIG. 7, (A)). Then, the amplitude calculating unit 23 sequentially fetches the amplitude value derived from the heartbeat of the subject, and that assisted by the IABP from each cardiac cycle, and produces an oscillation table (data string) indicating relationships between the elapsed time and the change of the amplitude value (FIG. 7, (B)).

Figure 6:
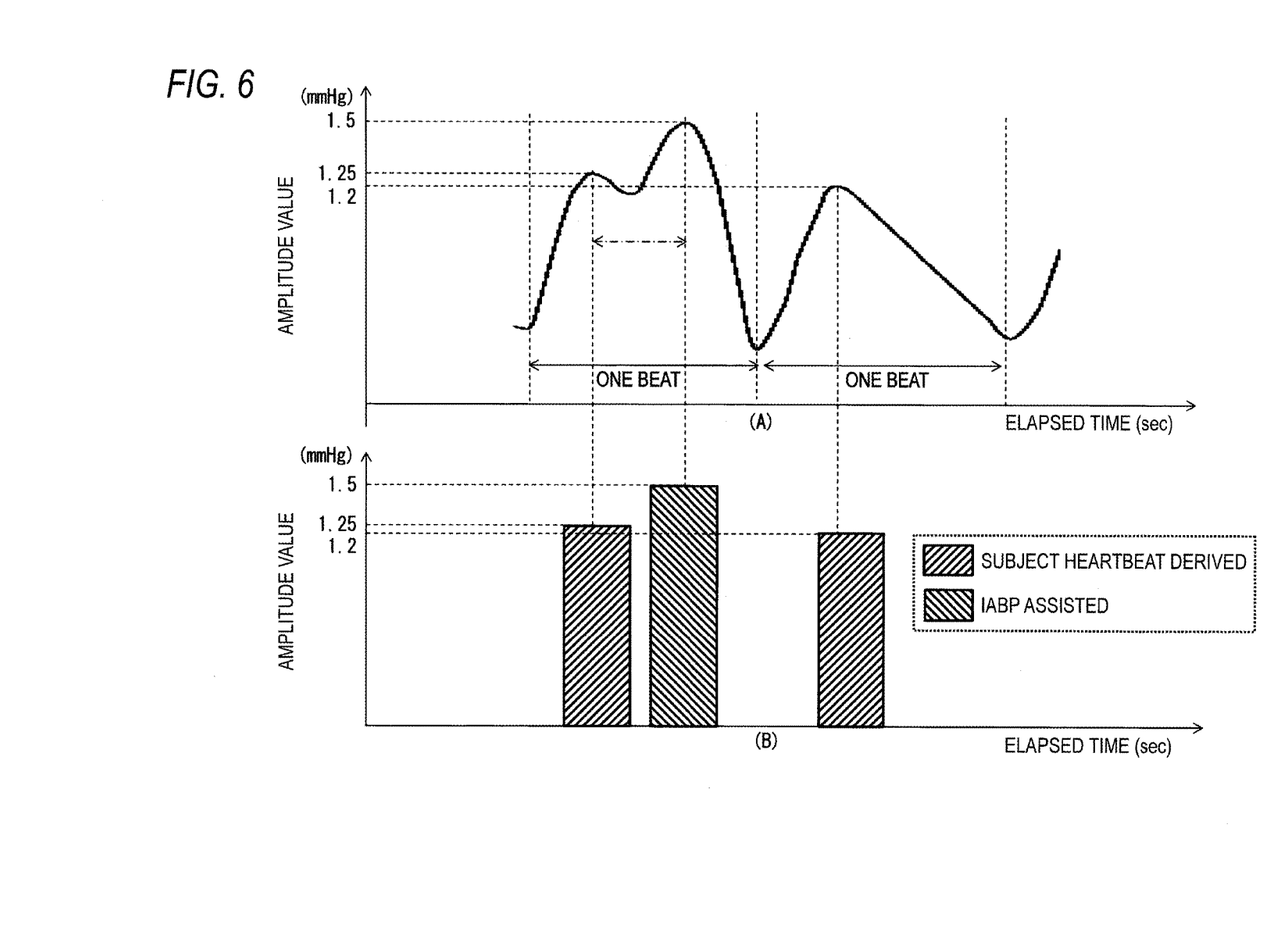
FIG. 6 is a diagram illustrating (A) an oscillation waveform with an IABP assist ratio of 1:2 (B) a calculation of amplitude values.
Figure 7:
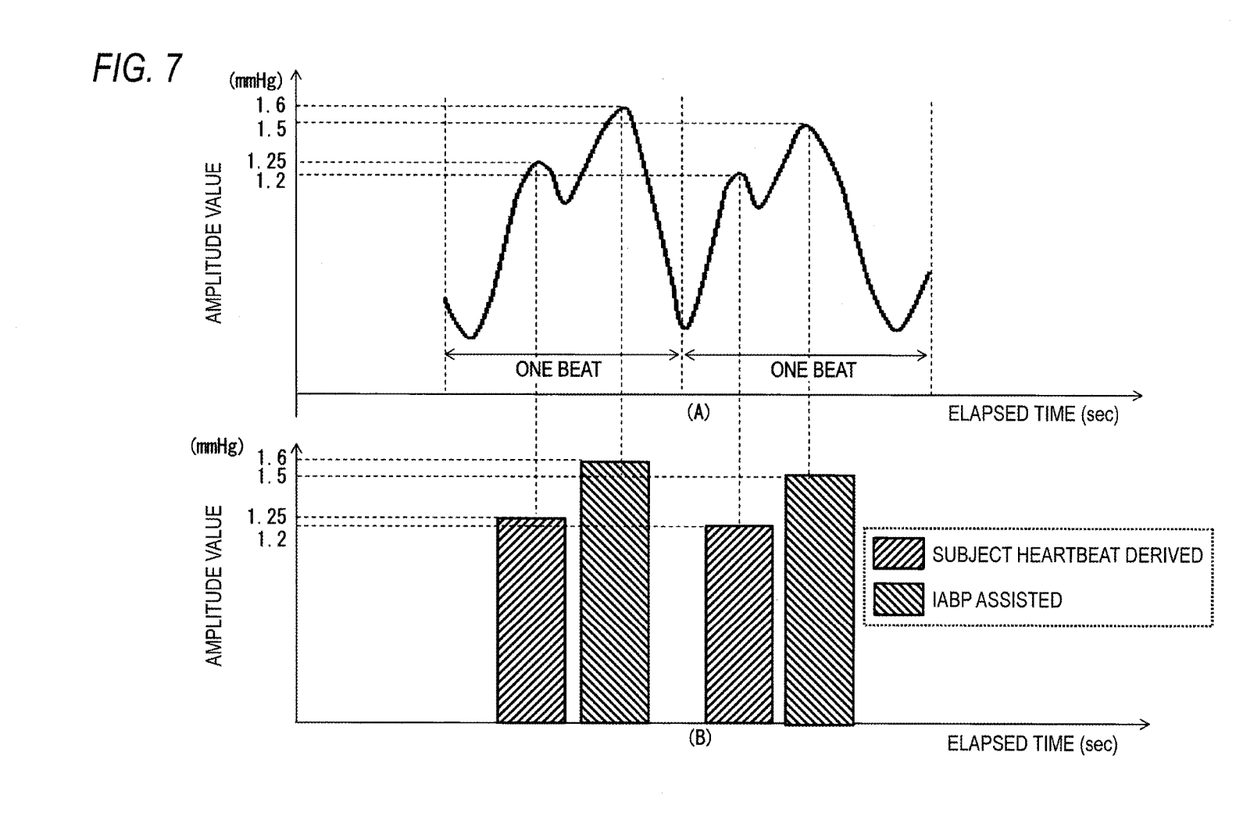
FIG. 7 is a diagram illustrating (A)) an oscillation waveform with the IABP assist ratio of 1:1 and (B) a calculation of amplitude values.

The amplitude calculating unit 23 supplies the produced oscillation table (data string) (the amplitude value derived from the heartbeat of the subject or that assisted by the IABP shown in (B) of FIGS. 6 and 7) to the blood pressure calculating unit 24. In the case where the doctor or the like designates by using the input unit 17 that the blood pressure value based on the amplitude value derived from the heartbeat of the subject is to be output, the amplitude calculating unit 23 may output only the oscillation table (data string) relating to the amplitude value derived from the heartbeat of the subject. Also in the case where the doctor or the like designates that the amplitude value assisted by the IABP is to be output, a similar output operation is performed.

The amplitude calculating unit 23 supplies also information of the cuff pressure which is input from the pulse wave detecting unit 21, to the blood pressure calculating unit 24.

A user of the biological information measuring apparatus 1 (e.g., a doctor) may input mode information explicitly indicating whether the IABP is being used or not, to the biological information measuring apparatus 1. In this case, the user operates the input unit 17 to input the mode information. Preferably, the mode information contains information of the IABP assist ratio. In the case where a ratio of 1:3 is input as the assist ratio, when the amplitude calculating unit 23 detects two maximal values in certain one cardiac cycle, for example, the calculation is performed so as to detect only one maximal value in two subsequent cardiac cycles. As described above, the assist ratio is explicitly input, and therefore the amplitude calculating unit 23 can calculate amplitude values more adequately (in other words, without causing erroneous detection).

In the case where two maximal values are detected in one cardiac cycle, the amplitude calculating unit 23 may calculate also the time period between the timing of detecting the first maximal value and that of calculating the second maximal value. In this case, the amplitude calculating unit 23 determines whether the difference between the calculated time period (time period between the detection timing of the first maximal value and that of the second maximal value, i.e., the portion indicated by the dash-dot line in (A) in FIG. 6) and a predetermined time period is within a given range or not. The predetermined time period is a preferable time period (when high effects of treatment are achieved) from the unassisted systolic pressure in the IABP treatment to the augmentation pressure. Therefore, the amplitude calculating unit 23 may have a function of, if the difference is not within the given range, determining that the treatment timing of the IABP (operation timing of the balloon) is not adequate, and notifying this to the user.

The blood pressure calculating unit 24 calculates a desired blood pressure value from relationships between the amplitude values calculated by the amplitude calculating unit 23 (i.e., the above-described oscillation table ((B) in FIGS. 6 and 7)) and the change of the pressurizing force of the cuff 11. The method of calculating the blood pressure value will be described in detail with reference to FIG. 8.

Figure 8:
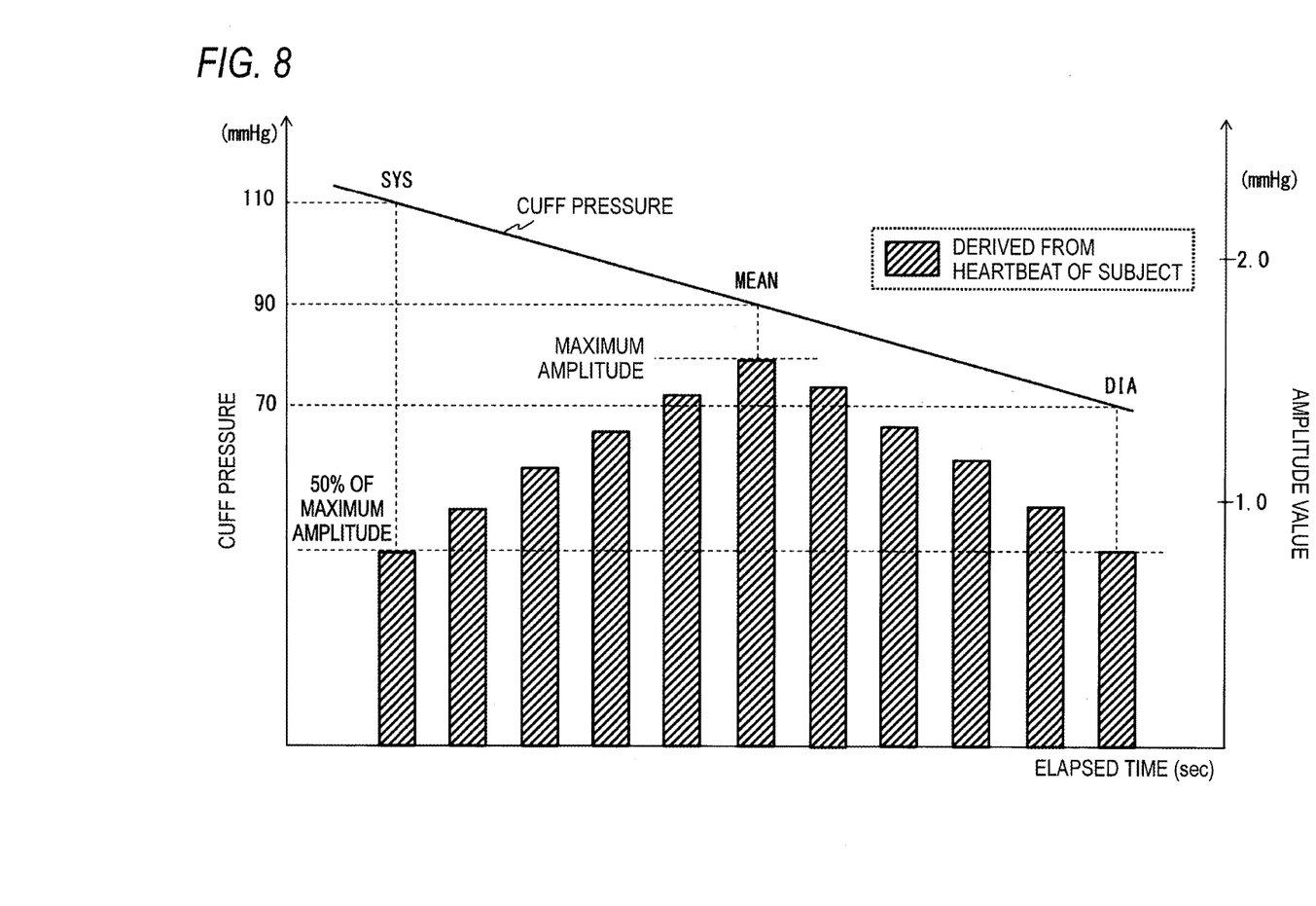
FIG. 8 is a conceptual diagram showing relationships between an oscillation table (data string) calculated by an amplitude calculating unit of the biological information measuring apparatus and a change of the cuff pressure.

FIG. 8 is a conceptual diagram showing the relationships between the oscillation table (data string) calculated by the amplitude calculating unit 23, and the change of the cuff pressure. An oscillation table (data string) corresponding to the output mode (the mode of outputting the blood pressure value derived from the heartbeat of the subject, that of outputting the blood pressure value assisted by the IABP, or that of outputting both the blood pressure values) designated by the doctor or the like is used as a target. In the example of FIG. 8, it is assumed that the doctor or the like selects the mode of outputting the blood pressure value derived from the heartbeat of the subject, and therefore the oscillation table (data string) derived from the heartbeat of the subject (values due to the heartbeat of the subject) is a target.

The blood pressure calculating unit 24 calculates the cuff pressure value corresponding to the maximum value of the amplitude, as the mean arterial pressure (MAP). Alternatively, the mean arterial pressure (MAP) may be obtained by an arbitrary process such as interpolation. In the example of FIG. 8, the cuff pressure value corresponding to the maximum value of the amplitude is 90 mmHg, and therefore the blood pressure calculating unit 24 calculates the mean arterial pressure (MAP) as 90 mmHg. The blood pressure calculating unit 24 further calculates the systolic pressure (SYS) and the diastolic pressure (DIA), from the cuff pressure corresponding to the amplitude value which is 50% of the maximum amplitude value. In the example of FIG. 8, the blood pressure calculating unit 24 calculates the systolic pressure (SYS) as 110 mmHg, and the diastolic pressure (DIA) as 70 mmHg.

With respect to the details of the method of calculating the blood pressure by using the oscillation table (data string), see, e.g., FIG. 1 of Takashi Usuda et al, "A blood Pressure Monitor with Robust Noise Reduction System under Linear Cuff Inflation and Deflation", Conf Proc IEEE Eng Med Biol Soc, 2010. The above-described blood pressure calculating method is the example in which an oscillation table (data string) produced by the oscillometric method is used. It is a matter of course that another method may be used. Although, in the above description, the systolic pressure (SYS) and the diastolic pressure (DIA) are calculated with respect to 50% of the maximum amplitude value, the value of 50% is a mere example.

Figure 9:
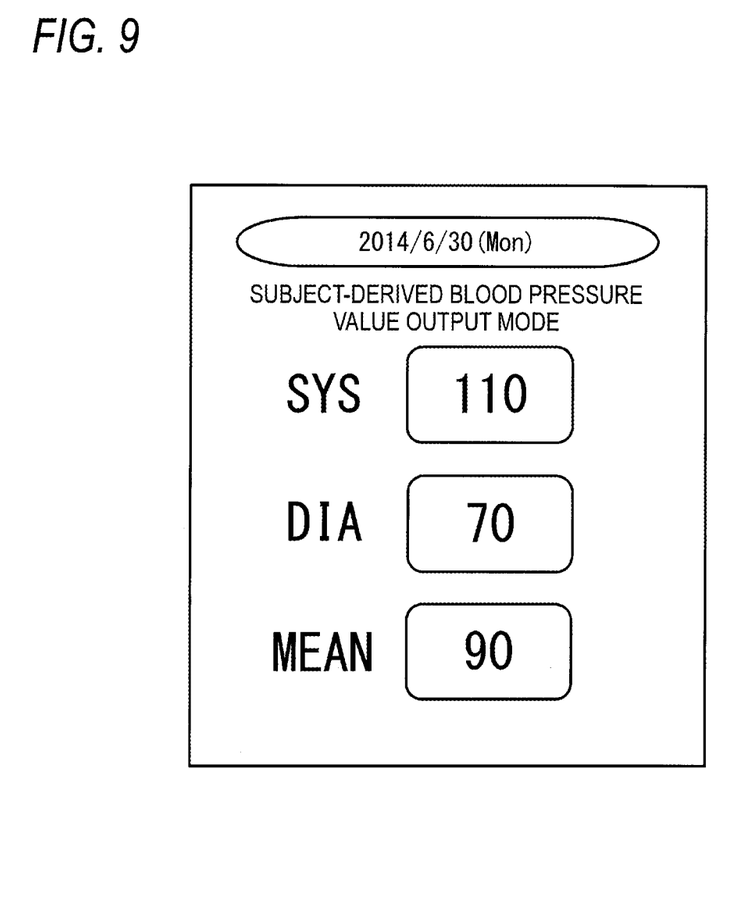
FIG. 9 is a view showing an example of an output screen of an output unit of the biological information measuring apparatus.

The blood pressure calculating unit 24 outputs the calculated blood pressure values through the output unit 16. FIG. 9 is a conceptual diagram showing an output example. As shown in FIG. 9, for example, the blood pressure calculating unit 24 outputs blood pressure values together with the output mode (e.g., printed on paper, or displayed on the display disposed on the housing of the biological information measuring apparatus 1). The screen example of FIG. 9 is a mere example, and the blood pressure values may be displayed together with the pulse wave and the ECG waveform.

Modifications

As a modification, a method of calculating the blood pressure value in which attention is focused on the volume of the blood flow circulating in the body of the subject will be described. In the above, the method in which at least one of the amplitude value derived from the heartbeat of the subject, and that assisted by the IABP is calculated has been described. In the following example, a method of measuring the blood pressure value in which both pulsation derived from the heartbeat of the subject, and that assisted by the IABP are considered will be described.

The processes of the pulse wave detecting unit 21 and the electrocardiogram measuring unit 22 are similar to those of above-described method. The amplitude calculating unit 23 detects the maximal value in each cardiac cycle from the oscillation waveform, in the above-described method, and obtains a moving average of the detected maximal values (e.g., a three-point moving average or a five-point moving average). That is, the amplitude calculating unit 23 calculates the amplitude values derived from the blood flow volume (amplitude values derived from the volume of the blood flow circulating in the body of the subject) by a moving average based on both the amplitude value derived from the heartbeat of the subject, and that assisted by the IABP. The amplitude calculating unit 23 produces an oscillation table (data string) by using the amplitude value obtained by a moving average. The oscillation table (data string) is produced in a method similar to the methods shown in FIGS. 6(B) and 7(B).

Preferably, the moving average is a calculation in which the IABP assist ratio is considered. In the case where the IABP assist ratio is 1:3, for example, it is preferable to perform a three-point moving average, and, in the case where the assist ratio is 1:5, for example, it is preferable to perform a five-point moving average. That is, the amplitude calculating unit 23 preferably performs an averaging process in which the number of data corresponds to the IABP assist ratio. In the case where a five-point moving average is performed in the case of the assist ratio of 1:3, for example, a case may occur where the averaging process is performed while two data assisted by the IABP are included in the five data. Similarly, a case may occur where the averaging process is performed while only one data assisted by the IABP is included in the five data. In both the cases, the accuracy of the calculated blood pressure value is slightly impaired. When the assist ratio and the number of processed data in the averaging process are corresponded to each other, however, the timing of the IABP is correctly reflected, and a more correct blood pressure value can be calculated. The case where the assist ratio and the number of processed data in the averaging process are corresponded to each other is a concept including not only the case where, when the assist ratio is 1:3, the averaging process is performed by using three data, but also the case where the averaging process is performed by using data the number of which is a multiple of three. The control unit 20 may perform the averaging process by applying the technique disclosed in JP5229449B2. The process after the production of the oscillation table (data string) is similar to that of the above-described method.

In the case where the blood pressure value is calculated based on the amplitude value obtained by a moving average of maximal values as described above, it is possible to acquire the blood pressure value to which the volume of blood circulating in the body of the subject is reflected, irrespective of whether the assist of the IABP is performed or not.

Figure 10:
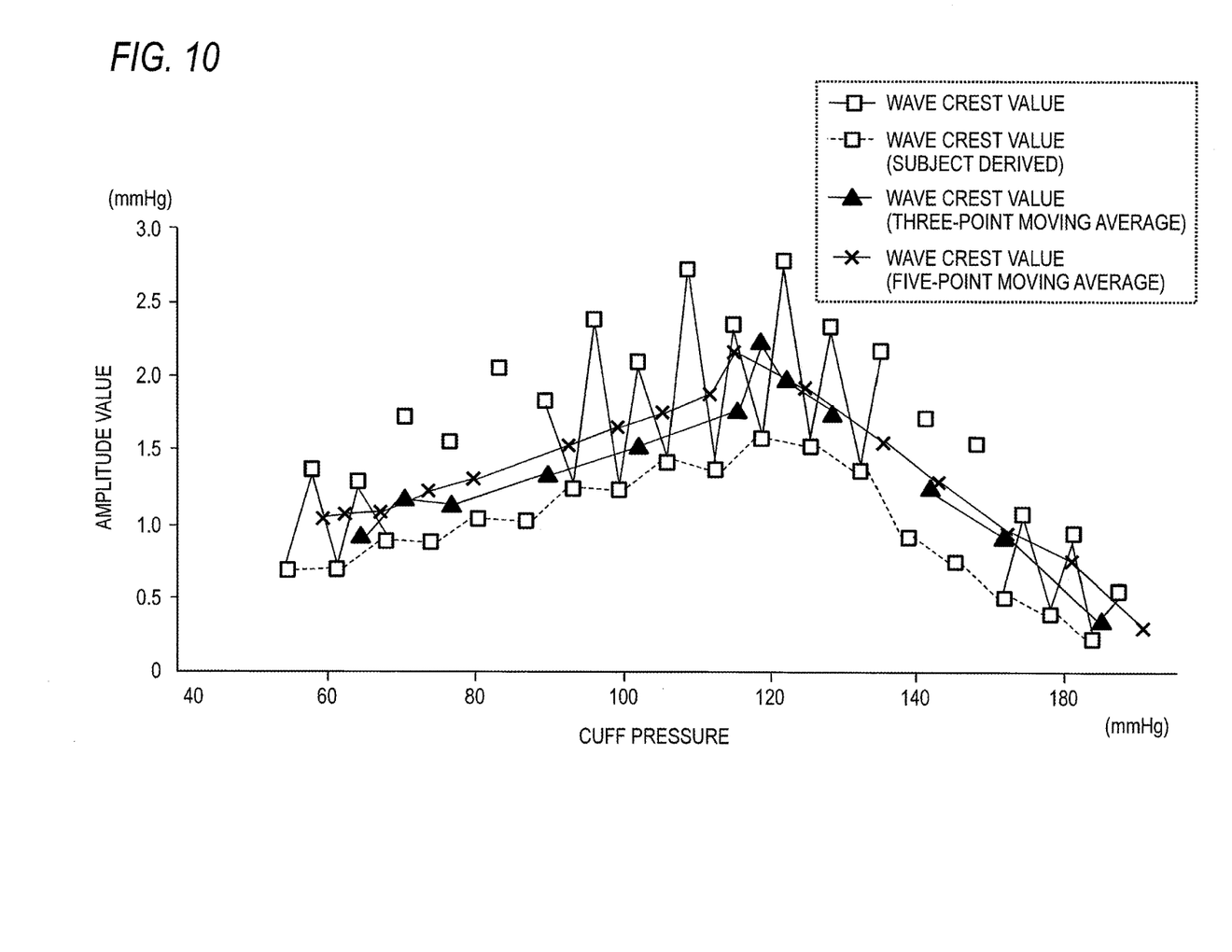
FIG. 10 is a view showing transitions of wave crest values.

Alternatively, the amplitude calculating unit 23 may perform a similar process by using the wave crest value ("height" in FIG. 4). FIG. 10 is a view showing the wave crest value (identical with that of FIG. 4) in the case where the assist ratio is 1:2, and various wave crest values. In the wave crest values obtained from the oscillation waveform (transition of wave crest values respectively enclosed by rectangles in the figure), as illustrated, the wave crest value derived from the heartbeat of the subject, and that assisted by the IABP appear alternately. Therefore, the process of detecting the above-described amplitude value derived from the heartbeat of the subject (the first maximal value in one cardiac cycle is detected as the amplitude value derived from the heartbeat of the subject) corresponds to the transition (the broken line in the figure) of the wave crest value which is formed by connecting together the lower-side peaks of the wave crest value. The wave crest value derived from the heartbeat of the subject (the broken line in FIG. 10), and the oscillation table (data string) shown in FIG. 8 and the like are produced based on the same oscillation waveform, and therefore in corresponding relationships with each other. Consequently, the amplitude calculating unit 23 may calculate also blood pressure values derived from the heartbeat of the subject based on the transition of the wave crest value.

The amplitude calculating unit 23 may calculate blood pressure values by using a moving average of wave crest values (a three-point moving average or five-point moving average in the example of FIG. 10). In this case, the amplitude values derived from the heartbeat of the subject, and those assisted by the IABP are handled after being averaged. The amplitude calculating unit 23 performs a calculating process based on the wave crest value obtained by the moving average, whereby blood pressure values corresponding to the blood flow volume in a predetermined time period can be calculated.

Then, effects of the biological information measuring apparatus 1 of the exemplary embodiment will be described. As described above, the biological information measuring apparatus 1 calculates at least one of the amplitude value derived from the heartbeat of the subject, that assisted by the IABP, and that obtained in the case where attention is focused on the blood flow volume, in accordance with the detection of the maximal value of the pulse waves in one cardiac cycle (whether two maximal values exist or not, and the detected amplitude value). The biological information measuring apparatus 1 can calculate a desired blood pressure value based on the amplitude values. In the case where the blood pressure value derived from the heartbeat of the subject (that corresponding to the pulsation of the heart of the subject) is to be referred, for example, the biological information measuring apparatus 1 calculates the blood pressure value by using the amplitude value derived from the heartbeat of the subject. When referring the blood pressure value derived from the pulsation of the heart of the subject, the doctor or the like can easily determine effects of the IABP treatment or weaning from the IABP.

The biological information measuring apparatus 1 detects a cardiac cycle based on the timing of detecting the QRS wave of an ECG. The R wave of an ECG shows a point where the voltage is largely changed. When the R wave is used as the reference, therefore, the biological information measuring apparatus 1 can accurately calculate the cardiac cycle. Therefore, the blood pressure value can be accurately calculated.

As described above, the amplitude calculating unit 23 detects the first maximal value in one cardiac cycle where two maximal values appear, as the amplitude value derived from the heartbeat of the subject (according to the operation of the heart of the subject) (FIG. 6, (A)). The amplitude calculating unit 23 further detects the second maximal value in one cardiac cycle where two maximal values appear, as the amplitude value assisted by the IABP (FIG. 6, (B)). The timing of detecting the maximal value (during a use of the IABP, two timings in one cardiac cycle, and, during a non-use of the IABP, one timing in one cardiac cycle) is consistent from person to person. With respect to any kind of subject, therefore, the blood pressure value can be calculated above a certain performance level.

Preferably, the amplitude calculating unit 23 may calculate blood pressure values by using the mode information (indicating whether the IABP is being used or not, and information of the assist ratio) which is explicitly designated. By having the assist ratio in advance, the amplitude calculating unit 23 can determine timings when two maximal values appear in one cardiac cycle. In this manner, likelihood of erroneous detection of amplitude value by the amplitude calculating unit 23 can be remarkably reduced.

While the present invention has been described with reference to certain exemplary embodiments thereof, the scope of the present invention is not limited to the exemplary embodiments described above, and it will be understood by those skilled in the art that various changes and modifications may be made therein without departing from the scope of the present invention as defined by the appended claims.

In the above description (FIG. 8 and the like), for example, it is assumed to use the oscillometric method in which the cuff 11 is pressurized to a given value and then depressurized. The invention is not limited to this method. The biological information measuring apparatus 1 may use the technique in which the non-invasive blood pressure (NIBP) is measured during pressurization (see, e.g., JP2012-040088A and www.nihonkohden.co.jp/iryo/products/monitor/01_bedside/bsm1700.html accessible as of Jun. 30, 2014). Also in this case, when the above-described algorithm (algorithm using detection of the maximal value) is used, a desired blood pressure (the blood pressure value derived from the heartbeat of the subject, that assisted by the IABP, or that derived from the blood flow volume of the subject) can be correctly acquired.

In the example described above, the cardiac cycle is calculated by using the ECG. The invention is not limited to this. The ECG is used for obtaining information (heartbeat information) relating to the pulsation (heartbeat) of the heart. Therefore, a configuration other than the electrocardiogram measuring unit 22 may be employed in so far as the configuration can obtain heartbeat information relating to the heartbeat of the subject. For example, the pulse wave may be detected by using an SpO2, and a cardiac cycle may be estimated from the pulse wave to perform the process described above. That is, the biological information measuring apparatus 1 has a pulsation information detecting unit configured to obtain heartbeat information of the subject (an ECG in the example of FIG. 1). The electrocardiogram measuring unit 22 is a mode of the pulsation information detecting unit.

The processes in the control unit 20 may be implemented by computer programs which operate in the biological information measuring apparatus 1. That is, the biological information measuring apparatus 1 includes also a configuration which has a usual computer, such as a central processing unit (CPU) and a memory device.

The programs may be stored in a non-transitory computer readable medium of any one of various types, and then supplied to the computer. The non-transitory computer readable medium includes tangible storage media of various types. Examples of the non-transitory computer readable medium are a magnetic recording medium (e.g., a flexible disk, a magnetic tape, and a hard disk drive), a magneto-optical recording medium (e.g., a magneto-optical disk), a CD-read only memory (CD-ROM), a CD-R, a CD-R/W, a semiconductor memory (e.g., a mask ROM, a programmable ROM (PROM), an erasable PROM (EPROM), a flash ROM, and a random access memory (RAM)). Alternatively, the programs may be supplied to the computer by means of a transitory computer readable medium of any one of various types. Examples of the transitory computer readable medium are an electrical signal, an optical signal, and an electromagnetic wave. The transitory computer readable medium can supply the programs to the computer through a wired communication path such as a metal wire or an optical fiber, or a wireless communication path.

What is claimed is:

1. A biological information measuring apparatus comprising:
    a pulsation information detecting unit configured to detect heartbeat information relating to a heartbeat of a subject;
    a pulse wave detecting unit configured to detect a pulse wave of the subject during a time period in which a cuff is inflated to pressurize a portion of the subject and during a time period in which the cuff is deflated to depressurize the portion of the subject;
    an amplitude calculating unit configured to detect a cardiac cycle of a heart from the heartbeat information and a maximal value of the pulse wave in each cardiac cycle, and to calculate, based on the maximal value detected from the pulse wave, at least one of an amplitude value derived from the heartbeat of the subject, an amplitude value assisted by an intra-aortic balloon pump (IABP), and an amplitude value derived from a blood flow volume of the subject; and
    a blood pressure calculating unit configured to calculate a blood pressure value from a relationship between the at least one of the amplitude value derived from the heartbeat of the subject, the amplitude value assisted by the IABP, and the amplitude value derived from a blood flow volume of the subject calculated by the amplitude calculating unit and a pressurizing force of the cuff.

2. The biological information measuring apparatus according to claim 1, wherein the heartbeat information is an electrocardiogram, and
    wherein the amplitude calculating unit is configured to detect a QRS wave from the electrocardiogram and to calculate amplitude values with reference to a detection point of the QRS wave.

3. The biological information measuring apparatus according to claim 2, wherein the amplitude calculating unit is configured to calculate, in a case where two maximal values exist in the detected cardiac cycle, a first maximal value as the amplitude value derived from the heartbeat of the subject and a second maximal value as the amplitude value assisted by the IABP, with reference to a peak value on a descending side of the pulse wave within a given time period from the detection point of the QRS wave.

4. The biological information measuring apparatus according to claim 1, wherein the amplitude calculating unit is configured to perform an averaging process on the detected maximal values to calculate the amplitude value derived from the blood flow volume of the subject.

5. The biological information measuring apparatus according to claim 4, wherein the amplitude calculating unit performs the averaging process using a number of data that corresponds to an assist ratio of the IABP.

6. The biological information measuring apparatus according to claim 4, wherein the averaging process is a moving average.

7. The biological information measuring apparatus according to claim 1, further comprising an input unit through which mode information is input, the mode information indicating whether the IABP is being used on the subject, and
    wherein the amplitude calculating unit detects the maximal value of the pulse wave based on the mode information.

8. The biological information measuring apparatus according to claim 1, wherein, in a case where two maximal values exist in the detected one cardiac cycle, the amplitude calculating unit determines whether an operation timing of the IABP is normal, based on a time interval between the two maximal values.

9. A biological information measuring method comprising:
    detecting heartbeat information relating to a heartbeat of a subject;
    detecting a pulse wave of the subject during a time period in which a cuff is inflated to pressurize a portion of the subject and during a time period in which the cuff is deflated to depressurize the portion of the subject;
    detecting a cardiac cycle of a heart from the heartbeat information and a maximal value of the pulse wave in each cardiac cycle;
    calculating, at least one of an amplitude value derived from the heartbeat of the subject, an amplitude value assisted by an intra-aortic balloon pump (IABP), and an amplitude value derived from a blood flow volume of the subject, based on the maximal value detected from the pulse wave; and calculating a blood pressure value from a relationship between the at least one of the amplitude value derived from the heartbeat of the subject, the amplitude value assisted by the IABP, and the amplitude value derived from a blood flow volume of the subject and a pressurizing force of the cuff.

10. A non-transitory computer readable medium storing a program that, when executed by a computer, causes the computer to execute a method comprising:

detecting heartbeat information relating to a heartbeat of a subject;

detecting a pulse wave of the subject during a time period in which a cuff is inflated to pressurize a portion of the subject and during a time period in which the cuff is deflated to depressurize the portion of the subject;

detecting a cardiac cycle of a heart from the heartbeat information and a maximal value of the pulse wave in each cardiac cycle;

calculating at least one of an amplitude value derived from the heartbeat of the subject, an amplitude value assisted by an intra-aortic balloon pump (IABP), and an amplitude value derived from a blood flow volume of the subject, based on the maximal value detected from the pulse wave; and calculating a blood pressure value from a relationship between the at least one of the amplitude value derived from the heartbeat of the subject, the amplitude value assisted by the intra-aortic balloon pump (IABP), and the amplitude value derived from a blood flow volume of the subject and a pressurizing force of the cuff.

* * * * *